(12) United States Patent
Kodama et al.

(10) Patent No.: US 7,731,960 B2
(45) Date of Patent: Jun. 8, 2010

(54) ANTIBODIES THAT INHIBIT TRANSPORT ACTIVITY OF PEPTIDE TRANSPORTERS

(75) Inventors: Tatsuhiko Kodama, Tokyo (JP); Takao Hamakubo, Tokyo (JP); Ryoichi Saitoh, Shizuoka (JP); Yoshiki Yamada, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/550,987

(22) PCT Filed: Mar. 26, 2004

(86) PCT No.: PCT/JP2004/004331

§ 371 (c)(1),
(2), (4) Date: May 25, 2006

(87) PCT Pub. No.: WO2004/087762

PCT Pub. Date: Oct. 14, 2004

(65) Prior Publication Data
US 2006/0210569 A1   Sep. 21, 2006

(30) Foreign Application Priority Data
Mar. 28, 2003 (WO) ............ PCT/JP03/03975
Apr. 15, 2003 (JP) ............ 2003-110898

(51) Int. Cl.
*A61K 39/395* (2006.01)
(52) U.S. Cl. .................................. 424/130.1
(58) Field of Classification Search .......... None
See application file for complete search history.

(56) References Cited

U.S. PATENT DOCUMENTS

| 5,500,346 | A | 3/1996 | Bright et al. |
| 5,849,525 | A | 12/1998 | Hediger |
| 6,270,978 | B1 | 8/2001 | Bright et al. |
| 6,713,278 | B1 | 3/2004 | Bouvier et al. |
| 6,867,017 | B1 | 3/2005 | Dean et al. |
| 2005/0004227 | A1 | 1/2005 | Saitoh |
| 2005/0222391 | A1 | 10/2005 | Kodama et al. |
| 2005/0281825 | A1 | 12/2005 | Kodama et al. |
| 2006/0084119 | A1 | 4/2006 | Saitoh et al. |
| 2006/0210569 | A1* | 9/2006 | Kodama et al. ......... 424/155.1 |
| 2008/0040820 | A1 | 2/2008 | Kodama et al. |

FOREIGN PATENT DOCUMENTS

| AU | 9676557 | 6/1997 |
| EP | 1142473 | 10/2001 |
| EP | 1 731 032 | 12/2006 |
| JP | 6-261761 | 9/1994 |
| JP | 8-134100 | 5/1996 |
| JP | 11-172 | 1/1999 |
| JP | 2001-197846 | 7/2001 |
| JP | 2001-139496 | 5/2005 |
| KR | 1999-0071666 | 9/1999 |
| WO | 97/19919 | 6/1997 |
| WO | WO 97/19919 | 6/1997 |
| WO | 98/46777 | 10/1998 |
| WO | 00/28016 | 5/2000 |
| WO | WO 03/033024 A1 | 4/2003 |
| WO | 03/047621 | 6/2003 |
| WO | 03/083116 | 10/2003 |
| WO | 03/104453 | 12/2003 |

OTHER PUBLICATIONS

Winter et al (Nature 1991;349:293-299).*
Campbell (Monoclonal Antibody Technology; 1984; Elsevier Science Publishing Company Inc: pp. 1-33).*
Liang, R. et al., "Human Intestinal H+/Peptide Cotransporter", J. Biol. Chem., 270:6456-63 (1995).
Liu, W. et al., "Molecular cloning of PEPT 2, a new member of the H+/peptide cotransporter family, from human kidney", Biochim. Biophys. Acta, 1235:461-6 (1995).
Basu et al., "Development and Utility of Anti-PepT1 Anti-Peptide Polyclonal Antibodies", Pharm. Res., 15:338-342 (1998).
Blissard et al., "Location, Sequence, Transcriptional Mapping, and Temporal Expression of the gp64 Envelope Glycoprotein Gene of the *Orgyia pseudotsugata* Multicapsid Nuclear Polyhedrosis Virus", Virology, 170:537-555 (1989).
Friedman et al., "Passive and Carrier-Mediated Intestinal Absorption Components of Two Angiotensin Converting Enzyme (ACE) Inhibitor Prodrugs in Rats: Enalapril and Fosinopril", Pharm. Res., 6:1043-1047 (1989).
Friedman et al., "Characterization of the Intestinal Transport Parameters for Small Peptide Drugs", J. Controlled Release, 13:141-146 (1990).
Ganapathy et al., "Proton-coupled solute transport in the animal cell plasma membrane", Curr. Opin. Cell Biol., 3:695-701 (1991).
Gonzalez et al., "An Oligopeptide Transporter is Expressed at High Levels in the Pancreatic Carcinoma Cell Lines AsPc-1 and Capan-2", Cancer Res., 58:519-525 (1998).
Higgins, "ABC Transporters: From Microorganisms to Man", Annu. Rev. Cell Biol., 8:67-113 (1992).
Knutter et al., "A Novel Inhibitor of the Mammalian Peptide Transporter PEPT1", Biochemistry, 40:4454-4458 (2001).
Lee et al., "Biopharmaceutics of transmucosal peptide and protein drug administration: role of transport mechanisms with a focus on the involvement of PepT1", J. Controlled Release, 62:129-140 (1999).
Lindley et al., "Production of monoclonal antibodies using recombinant baculovirus displaying gp64-fusion proteins", J. Immunol. Methods, 234:123-135 (2000).

(Continued)

*Primary Examiner*—Misook Yu
(74) *Attorney, Agent, or Firm*—Fish & Richardson P.C.

(57) ABSTRACT

The present inventors discovered that the PepT-binding antibodies have the ability to inhibit the transport activity of peptide transporters, as a result of dedicated research. These antibodies may be utilized as cell growth inhibitors, for example, for treating and preventing cancer.

10 Claims, 8 Drawing Sheets

OTHER PUBLICATIONS

Loisel et al., "Recovery of homogeneous and functional β,-adrenergic receptors from extracellular baculovirus particles", Nat Biotechnol., 12:1300-1304 (1997).

Mangor et al, "A GP64-Null Baculovirus Pseudotyped with Vesicular Stomatitis Virus G Protein", J. Virol., 75:2544-2556 (2001).

Mikhailov et al., "Expression of functionally active ATP-sensitive K-channels in insect cells using baculovirus", FEBS Lett., 429:390-394 (1998).

Mrsny, "Oligopeptide Transporters as Putative Therapeutic Targets for Cancer Cells", Pharm. Res., 15:816-818 (1998).

Muranushi et al., "Transport Characteristics of Ceftibuten, a New Oral Cephem, in Rat Intestinal Brush-Border Membrane Vesicles: Relationship to Oligopeptide and Amino β-Lactam Transport", Pharm. Res., 6:308-312.

Nakanishi et al., "Cancer Cell-Targeted Drug Delivery Utilizing Oligopeptide Transport Activity", Int. J. Cancer, 88:274-280 (2000).

Nakashima et al., "Kinetics and Mechanism of In Vitro Uptake of Amino-β-Lactam Antibiotics by Rat Small Intestine and Relation to the Intact-peptide Transport System", Biochem. Pharmacol., 33:3345-3352 (1984).

Noe et al., "Characterization of the Mouse Bile Salt Export Pump Overexpressed in the Baculovirus System", Hepatology, 33:1223-1231 (2001).

Ogihara et al., "Immuno-Localization of $H^+$/Peptide Cotransporter in Rat Digestive Tract", Biochem. Biophys. Res. Commun., 220:848-852 (1996).

Okano et al., "$H^+$ Coupled Uphill Transport of Aminocephalosporins via the Dipeptide Transport System in Rabbit Intestinal Brush-border Membranes", J. Biol. Chem., 261:14130-14134 (1986).

Sai et al., "Immunolocalization and pharmacological relevance of oligopeptide transporter PepT1 in intestinal absorption of β-lactam antibiotics", FEBS Lett., 392:25-29 (1996).

Sai et al., "Selective Delivery of Peptide Anticancer Drugs Via Oligopeptide Transporter Expresssed in Cancer Cells", Millennial World Congress of Pharamaceutical Sciences, 61:2-2124 (2000).

Saito et al., "Cloning and Characterization of a Rat $H^+$/peptide Cotransporter Mediating Absorption of β-Lactam Antibiotics in the Intestine and Kidney", J. Pharmacol. Exp. Ther., 275:1631-1637 (1995).

Saito el al., "Molecular cloning and tissue distribution of rat peptide transporter PEPT2", Biochim. Biophys. Acta., 1280:173-177 (1996).

Sakaguchi et al., "The Ion Channel activity of the Influenza Virus $M_2$ Protein Affects Transport through the Golgi Apparatus", J. Cell. Biol., 133:733-747 (1996).

Satoi et al., "Genetic Immunization of Wild-Type and Hepatitis C Virus Transgenic Mice Reveals a Hierarchy of Cellular Immune Response and Tolerance Induction against Hepatitis C Virus Structural Proteins", J. Virol., 75:12121-12127 (2001).

Shen et al., "Localization of PEPT1 and PEPT2 proton-coupled oligopeptide transporter mRNA and protein in rat kidney", Am. J. Physiol., 276:F658-665 (1999).

Steiner et al., "The PTR family: a new group of peptide transporters", Mol. Microbiol., 16:825-834 (1995).

Strehlow et al., "Retroviral membrane display of apoptotic effector molecules", Proc. Natl. Acad. Sci. USA, 97:4209-4214 (2000).

Sugano et al., "Quantitative Structure-Intestinal Permeability Relationship of Benzamidine Analogue Thrombin Inhibitor", Bioorg. Med. Chem. Lett. 10:1939-1942 (2000).

Sun et al., "Drug Inhibition of Gly-Sar Uptake and hPepT1 Localization using hPepT1-GFP Fusion Protein", AAPS Pharmsci., 3:1-9 (2001).

Szakacs et al., "Characterization of the ATPase Cycle of Human ABCA1: Implications for its Function as a Regulator Rather Than an Active Transporter", Biochem. Biophys. Res. Commun., 288:1258-1264 (2001).

Takahashi et al., "Interaction of β-Lactam Antibiotics with $H^+$/peptide Cotransporters in Rat Renal Brush-Border Membranes", J. Pharmacol. Exp. Ther., 286:1037-1042 (1998).

Terada et al., "Peptide Transporter Family", Tanpakushitsu Kakusan Koso., 46:621-628 (2001) (English summary provided).

Terada et al., "Characterization of Stably Transfected Kidney Epithelial Cell Line Expressing Rat $H^+$/Peptide Cotransporter PEPT1: Localization of PEPT1 and Transport of β-Lactam Antibiotics", J. Pharmacol. Exp. Ther., 281:1415-1421 (1997).

Zhou et al., "Characterization of an oligopeptide transporter in renal lysosomes", Biochim. Biophys. Acta., 1466:372-378 (2000).

Hsu et al., "Overexpression of Human Intestinal Oligopeptide Transporter in Mammalian Cells via Adenoviral Transduction," Pharm. Res., 15:1376-1381 (1998).

Basu et al., "Screening of Anti-PepT1 Antibodies Using Indirect ELISA," *Pharmaceutical Research*, 13(9 Suppl.):S-37, Abstract No. APQ 1137 (1996).

Houdebine, "Transgenic animal bioreactors," *Transgenic Res.*, 9:305-320 (2000).

Kolb et al., "Insertion of a foreign gene into the β-casein locus by Cre-mediated site specific recombination," *Gene*, 227:21-31 (1999).

Lariviere et al., "Transgenic Studies of Pain and Analgesia: Mutation or Background Genotype?" *J. Pharmacol Exp. Ther.*, 297:467-473 (2001).

Leiter, "Mice with targeted gene disruptions or gene insertions for diabetes research: problems, pitfalls, and potential solutions," *Diabetologia*, 45:296-308 (2002).

Mancini et al., "Induction of Anti-Hepatitis B Surface Antigen (HBsAg) Antibodies in HBsAg Producing Transgenic Mice: A Possible Way of Circumventing 'Nonresponse' to HBsAg," *J. Med. Virol.*, 39:67-74 (1993).

Murray, "Genetic Modification of Animals in the Next Century," *Theriogenology*, 51:149-159 (1999).

Sigmund, "Viewpoint: Are Studies in Genetically Altered Mice Out of Control," *Arterioscler. Thromb. Vasc. Biol.*, 20:1425-1429 (2000).

Tsuchiya, "Therapeutic Antibody," Presentation, Chugai Pharmaceutical Co., Ltd., 21 pages (Jan. 21, 2003).

Blissard et al., "Baculovirus gp64 Gene Expression: Analysis of Sequences Modulating Early Transcription and Transactivation by IE1," *J. Virol.*, 65:5820-5827 (1991).

Karaki et al., "Production of anti-HLA class 1 alloantibodies using HLA-B51 transgenic mice," *Nihonmenekigakkaisoukai Gakujutsushuukaikiroku*, Abstract No. C61, p. 197 (1990) (English translation included).

Nishimura et al., "Expression of the Human MHC, HLA-DQw6 Genes Alters the Immune Response in C57BL/6 Mice," *J. Immunol.*, 145:353-360 (1990).

Okamoto et al., "Generation of monoclonal antibodies directed against allotypic epitopes of HLA class II antigen by utilizing HLA-DQw6 transgenic mice," *Nihonmenekigakkaisoukai Gakujutsushuukaikiroku*, Abstract No. C62, p. 197 (1990) (English translation included).

D'Onofrie, "Making the case for acncer prevention in the schools", Journal of School Health 59(5):225-227, 1989.

Inoue et al., "Regulation of human peptide transporter 1 (PEPT1) in gastric cancer cells by anticancer drugs", Cancer Letters 230:72-80, 2005.

Pardee, "Tumor progression—targets for differential therapy", Journal of Cellular Physiology 209(3):589-591, 2006 (abstract only).

Braunagel et al., "Autographa califomica Nuclear Polyhedrosis Virus, PDV, and ECV Viral Envelopes and Nucleocapsids: Structural Proteins, Antigens, Lipid and Fatty Acid Profiles," Virology, 202:315-320 (1994).

Grabherr et al., "Developments in the use of baculoviruses for the surface display of complex eukaryotic proteins," Trends in Biotechnology, 19:231-236 (2001).

Marheineke et al., "Lipid composition of *Spodoptera frugiperda* (Sf9) and *Trichoplusia ni* (Tn) insect cells used for baculovirus infection," FEBS Letters, 441:49-52 (1998).

ATCC Web Catalog, "Tumor Cell Lines" www.atcc.org (2007), 15 pages.

Boublik et al., "Eukaryotic Virus Display: Engineering the major Surface Glycoprotein of the *Autographa californica* Nuclear Polyhedrosis Virus (ScNPV) for the Presentation of Foreign Proteins on the Virus Surface," *Biotechnology*, 13 1079-1084 (1995).

"Cancer Classification," SEER Training Website, www.training.seer. cancer.gov/module_cancer_disease/unti3-categories2_by_histology (2005), 3 pages.

Garcia et al., "cDNA Cloning of MCT2, A Second Monocarboxylate Transporter Expressed in Different Cells than MCT1," *The Journal of Biological Chemistry*, 270: 1843-1849 (1995).

Grever et al., "The National Cancer Institute: Cancer Drug Discovery and Development Program," Seminars in Oncology, 19(6): 622-638 (1992).

Hefferon et al., "Host Cell receptor Binding by Baculovirus GP64 and Kinetics of Virion Entry," Virology, 258: 455-468 (1999).

Kamada et al., "Generation of GP64-Expressing Mice and Induction of Tolerance to Budding Baculoviruses," Nihon Bunshi Seibutsu Gakkai Nenkai Program Koen Yoshishu, Abstract No. 1PC-162, 26:659 (2003) (Translation Provided).

Lu et al., "Characterization of a Truncated Soluble Form of the Baculovirus (AcMNPV) Major Envelope Protein Gp64," Protein Expression and Purification, 24: 196-201 (2002).

Miyasaka et al., "Characterization of Human Taurine Transported Expressed in Insect Cells Using a Recombinant Baculovirus," Protein Expression and Purification, 23: 389-397 (2001).

Monsma et al., "Identification of a Membrane Fusion Domain and an Oligomerization Domain in the Baculovirus GP64 Envelope Fusion Protein," *Journal of Virology*, 69: 2583-2595 (1995).

Monsma et al., "The GP64 Envelope Fusion Protein is an Essential Baculovirus Protein Required for Cell-to-Cell Transmission of Infection," *Journal of Virology*, 70: 4607-4616 (1996).

Ohtomo et al., "Generation of Functional Antibodies Using GP64-Expressing/CCR2 Knock-Out Mice and CCR2-Expressing Baculoviruses," Nihon Bunshi Seibutsu Gakkai Nenkai Program Koen Yoshishu, Abstract No. 1PC-164, 26: 660 (2003) (Translation Provided).

Sakaguchi T. et al., "The Ion Channel Activity of the Influenza Virus M2 Protein Affects Transport through the Golgi Apparatus", J Cell Biol., 133(4):733-747 (1996).

Seliger et al., "Analysis of the MHC Class I Antigen Presentation Machinery in Human Embryonal Carcinomas: Evidence for Deficiencies in TAP, LMC, and MHC Class I Expression and Their Upregulation by IFN-γ," Scandinavian Journal of Immunology, 46: 625-632 (1997) (Abstract).

Suzuki et al., "Effects of Retinoic Acid on Lung Smooth Muscle Cells," Meeting on Experimental Biology: Translating the Genome (Apr. 17-21, 2004) as published in *FASEB Journal*, 18(4-5): 355-356 (2004) (Abstract).

Tamura et al., "CD14 Transgenic Mice Expressing Membrane and Soluble Forms: Comparisons of Levels of Cytokines and Lethalities in Response to Lipopolysaccharide Between Transgenic and Non-Transgenic Mice," International Immunology, 11:333-339 (1999).

Watanabe et al., "Enhanced Immune Responses in Transgenic Mice Expressing a Truncated Form of the Lymphocyte Semaphorin CD100," *J. Immunol.* 167: 4321-4328 (2001).

Breyer et al., "Mutational analysis of ligand binding activity of $\beta_2$ adrenergic receptor expressed in *Escherichia coli,*" EMBO J., 9(9):2679-2684 (1990).

Clark, M., "Antibody humanization: a case of the 'Emperor's new clothes'?," *Immunol. Today*, 21(8):397-402 (2000).

Covitz et al., "Membrane Topology of the Human Dipeptide Transporter, hPEPT1, Determined by Epitope Insertions," *Biochemistry*, 37:15214-15221 (1998).

Kanamitsu, Kotai Kogaku Nyumon, 33-6 (1994) (English translation included).

Kawaguchi et al., "Gan Chiryo to Syukusyu: Frontiers in Cancer Treatment," 13(1):12-20 (2001).

McLaughlin, "Rituximab: perspective on single agent experience, and future directions in combination trials," *Critical Reviews in Oncology/Hematology*, 40:3-16 (2001).

Saitoh et al., "Recovery of functional peptide transporter PepT1 in budded baculovirus fraction," *Protein Expr. Purif.*, 46(1):130-135 (2006).

Tada et al., "Complement-dependent cytolysis," *Dictionary of Immunology 3rd Edition*, 144 (1993).

Tate et al., "Molecular Chaperones Stimulate the Functional Expression of the Cocaine-Sensitive Serotonin Transporter," *J. Biol. Chem.*, 274(25):17551-17558 (1999).

Tsuro et al., "Inhibition of Multidrug-resistant Human Tumor Growth in Athymic Mice by Anti-P-glycoprotein Monoclonal Antibodies," *Jpn. J. Cancer Res.*, 80:627-631 (1989).

Walker et al., "Substrate upregulation of the human small intestinal peptide transporter, hPepT1," *Journal of Physiology*, 507.3:697-706 (1998).

Fish & Richardson P.C., Response to Restriction Requirement dated Jun. 6, 2007 in U.S. Appl. No. 10/492,376, filed Jul. 6, 2007, 1 page.

Fish & Richardson P.C., Amendment in Reply to Action dated Sep. 17, 2007 in U.S. Appl. No. 10/492,376, filed Jan. 17, 2008, 10 pages.

Japanese Patent Office, International Preliminary Report on Patentability for App. Ser. No. PCT/JP02/10743, dated Apr. 21, 2003, 4 pages.

Japanese Patent Office, International Search Report for App. Ser. No. PCT/JP02/10743, mailed Feb. 4, 2003, 2 pages.

Fish & Richardson P.C., Response to Restriction Requirement dated Jun. 13, 2008 in U.S. Appl. No. 10/497,900, filed Jul. 11, 2008, 1 page.

Fish & Richardson P.C., Amendment in Reply to Action dated Sep. 19, 2007 in U.S. Appl. No. 10/497,900, filed Feb. 19, 2008, 9 pages.

Fish & Richardson P.C., Amendment in Reply to Action dated Oct. 30, 2008 in U.S. Appl. No. 10/497,900, filed Mar. 27, 2009, 8 pages.

USPTO Notice of Allowance in U.S. Appl. No. 10/497,900, dated Sep. 8, 2009, 7 pages.

Japanese Patent Office, International Preliminary Report on Patentability for App. Ser. No. PCT JP02/12708, dated Aug. 12, 2003, 6 pages.

Japanese Patent Office, International Search Report for App. Ser. No. PCT/JP02/12708, mailed Mar. 11, 2003, 4 pages.

Fish & Richardson P.C., Response to Restriction Requirement dated Jan. 25, 2007 in U.S. Appl. No. 10/509,343, filed Feb. 26, 2007, 6 pages.

Fish & Richardson P.C. Amendment in Reply to Action dated May 16, 2007 in U.S. Appl. No. 10/509,343, filed Nov. 16, 2007, 24 pages.

USPTO Interview Summary in U.S. Appl. No. 10/509,343, dated Mar. 6, 2008, 4 pages.

Fish & Richardson P.C. Amendment in Reply to Action dated Feb. 5, 2008 in U.S. Appl. No. 10/509,343, filed Mar. 5, 2009, 10 pages.

USPTO Notice of Allowance in U.S. Appl. No. 10/509,343, dated May 27, 2009, 17 pages.

USPTO Notice of Allowance in U.S. Appl. No. 10/509,343, dated Sep. 21, 2009, 7 pages.

Japanese Patent Office, International Preliminary Report on Patentability for App. Ser. No. PCT/JP03/03975, dated Sep. 8, 2003, 6 pages.

Japanese Patent Office, International Search Report for App. Ser. No. PCT/JP03/03975, mailed May 6, 2003, 2 pages.

Fish & Richardson P.C., Response to Restriction Requirement dated Dec. 28, 2005 in U.S. Appl. No. 10/516,603, filed Mar. 28, 2006, 1 page.

Fish & Richardson P.C., Amendment in Reply to Action dated Apr. 24, 2006 in U.S. Appl. No. 10/516,603, filed Oct. 24, 2006, 9 pages.

Fish & Richardson P.C., Supplemental Response to Amendment filed Oct. 24, 2006 in U.S. Appl. No, 10/516,603, filed Nov. 7, 2006, 5 pages.

Fish & Richardson P.C., Amendment in Reply to Action dated Mar. 9, 2007 in U.S. Appl. No. 10/516,603, filed Jun. 11, 2007, 10 pages.

Fish & Richardson P.C., Amendment in U.S. Appl. No. 10/516,603, filed Sep. 10, 2007, 6 pages.

USPTO Notice of Allowance in U.S. Appl. No. 10/516,603, dated Apr. 25, 2008, 11 pages.

Fish & Richardson P.C., Amendment in U.S. Appl. No. 10/516,603, filed Jul. 24, 2008, 5 pages.

Fish & Richardson P.C., Amendment in Reply to Action dated Jan. 27, 2009 in U.S. Appl. No. 10/516,603, filed May 15, 2009, 4 pages.

USPTO Office Action in U.S. Appl. No. 10/516,603, dated Aug. 19, 2009, 10 pages.

Japanese Patent Office, International Preliminary Report on Patentability for App. Ser. No. PCT/JP03/07071, dated Nov. 21, 2003, 7 pages.

Japanese Patent Office, International Search Report for App. Ser. No. PCT/JP03/07071, mailed Jul. 22, 2003, 3 pages.

Fish & Richardson P.C., Amendment in Reply to Action dated Oct. 16, 2008 in U.S. Appl. No. 10/594,690, filed Apr. 16, 2009, 9 pages.

USPTO Final Office Action in U.S. Appl. No. 10/594,690, mailed Jun. 8, 2009, 11 pages.

Japanese Patent Office, International Preliminary Report on Patentability for App. Ser. No. PCT/JP2005/006298, dated Feb. 8, 2006, 10 pages.

Japanese Patent Office, International Search Report for App. Ser. No. PCT/JP2005/006298, mailed Jul. 12, 2005, 3 pages.

European Search Report for App. Ser. No. EP 04723785.4, dated Jul. 12, 2006, 2 pages.

Japanese Patent Office, International Preliminary Report on Patentability for App. Ser. No. PCT/JP04/004331, dated Dec. 17, 2004, 5 pages.

Japanese Patent Office, International Search Report for App. Ser. No. PCT/JP04/004331, mailed Jun. 22, 2004, 2 pages.

European Search Report for App. Ser. No. EP 03 73 3287, dated Jun. 22, 2009, 2 pages.

Bachmann et al., "Correlation of Tolerogenicity of a Viral Antigen with Its Immunogenicity," *The Journal of Immunology*, 158:5106-5111 (1997).

Ramamoorthy et al., "Proton/peptide cotransporter (PEPT 2) from human kidney: Functional characterization and chromosomal localization," *Biochimica et Biophysica Acta*, 1240:1-4 (1995).

Steinhoff et al., "Variable Immune Response Against a Developmentally Regulated Self-Antigen," *Journal of Autoimmunity*, 12:27-34 (1999).

European Search Report for App. Ser. No. EP 05 72 7975, dated Sep. 11, 2009, 2 pages.

Renes et al., "ATP- and glutathione-dependent transport of chemotherapeutic drugs by the multidrug resistance protein MRP1 ," *Br. J. Pharmacol.*, 126:681-688 (1999).

Tabas et al., "A high-throughput assay for measurement of multidrug resistance protein-mediated transport of leukotriene C4 into membrane vesicles," *Anal. Biochem.*, 310:61-66 (2002).

Vivekananda et al., "Monoclonal antibodies as tools in membrane biochemistry. Identification and partial characterization of the dicarboxylate transporter from pea leaf mitochondria," *J. Biol. Chem.*, 263(10):4782-4788 (1988).

\* cited by examiner

SEQUENCE LISTING

<160> NUMBER OF SEQ ID NOS: 1

<210> SEQ ID NO 1
<211> LENGTH: 118
<212> TYPE: PRT
<213> ORGANISM: Mus musculus

<400> SEQUENCE: 1

```
Gly Gly Gly Gly Phe Gln Val Gln Leu Gln Gln Ser Gly Ala Glu Leu
1               5                   10                  15

Val Lys Pro Gly Ala Ser Val Lys Leu Ser Cys Lys Thr Ser Gly Phe
            20                  25                  30

Thr Phe Ser Ser Thr Tyr Ile Ser Trp Leu Lys Gln Lys Pro Gly Gln
        35                  40                  45

Ser Leu Glu Trp Ile Ala Trp Ile Phe Ala Gly Asp Gly Asn Thr Ile
    50                  55                  60

Tyr Asn Gln Lys Phe Thr Gly Lys Ala Gln Leu Thr Val Asp Thr Ser
65                  70                  75                  80

Ser Ser Thr Val Tyr Met Gln Phe Ser Ser Leu Thr Ile Glu Asp Ser
                85                  90                  95

Ala Ile Tyr Tyr Cys Ala Arg Gln Arg Arg Tyr Asp Tyr Asp Trp Phe
            100                 105                 110

Ala Tyr Trp Gly Gln Gly
            115
```

ANTIBODIES THAT INHIBIT TRANSPORT ACTIVITY OF PEPTIDE TRANSPORTERS

CROSS-REFERENCE TO RELATED APPLICATIONS

This application is the National Stage of International Application No. PCT/JP2004/004331, filed Mar. 26, 2004, which claims the benefit of International Application No. PCT/JP2003/03975, filed on Mar. 28, 2003, and Japanese Patent Application Serial No. 2003-110898, filed on Apr. 15, 2003. The contents of all of the foregoing applications are hereby incorporated by reference in their entireties.

TECHNICAL FIELD

The present invention relates to antibodies that inhibit the transport activity of peptide transporters, and to cell growth inhibitors comprising the antibodies as an active ingredient.

BACKGROUND ART

Mammalian animals need to incorporate nutrients from an external source, and many transport proteins are known to exist in cells. Peptide transporters (peptide transport proteins) transport peptides, and many have been found to date (for example, Non-Patent Documents 1, 2, and 3; and Patent Documents 1, 2, and 3). Peptide transporters can be classified into proteins that import peptides into cells, and proteins that export peptides from cells. They can also be classified by the difference of the energy sources used in transport. Proton-driven peptide transporters, which carry out transport by utilizing the difference in proton concentrations between the inside and outside of a cell, belong to the PTR family (Non-Patent Document 3). Peptide transporters that carry out transport using ATP in the body belong to the ABC family (Non-Patent Document 4).

It has been reported that peptide transporters are involved in the transport of not only small-molecule peptides such as dipeptides and tripeptides, but also pharmaceutical agents such as β-lactam antibiotics and ACE inhibitors (Non-Patent Documents 5, 6, 7, 8, 9, and 10).

PepT1 and PepT2 are proton-driven peptide transporters which contribute to the absorption of proteins and the maintenance of peptidic nitrogen sources through uptake of small-molecule peptides into cells. PepT1 and PepT2 are 12-transmembrane proteins, consisting of 708 and 729 amino acids, respectively (Non-Patent Documents 1, 2, and 11).

PepT1 and PepT2 have also been reported to transport pharmaceuticals such as β-lactam antibiotics and bestatin (Non-Patent Documents 12, 13, and 14).

PepT1 is mainly expressed in the small intestine, and its expression in kidney and pancreas has also been confirmed. PepT2 expression has been confirmed in kidney, brain, lung, and spleen. PepT1 and PepT2 have been reported to be localized in the small intestine, as well as in the brush border membrane of renal tubular epithelial cells (Non-Patent Documents 15, 16, 17, and 11).

Furthermore, overexpression of PepT1 in the cell membranes of human pancreatic ductal carcinoma cell lines (Non-Patent Document 18), and PepT2 mRNA expression in human pancreatic ductal carcinoma cell lines (Non-Patent Document 19) have been reported. However, the involvement of PepT1 and PepT2 in cancer cell growth is not clear, and the question of whether inhibiting the functions of PepT1 and PepT2 will affect cancer cell proliferation has never been discussed.

[Patent Document 1] Japanese Patent Application Kokai Publication No. (JP-A) H6-261761 (unexamined, published Japanese patent application)
[Patent Document 2] JP-A H11-172
[Patent Document 3] U.S. Pat. No. 5,849,525
[Non-Patent Document 1] J. Biol. Chem., 270(12):6456-6463, (1995)
[Non-Patent Document 2] Biochim. Biophys. Acta., 1235: 461-466, (1995)
[Non-Patent Document 3] Mol. Microbiol., Vol. 16, p825, (1995)
[Non-Patent Document 4] Annu. Rev. Cell. Biol., Vol. 8, p67, (1992)
[Non-Patent Document 5] Ganaphthy, Leibach., Curr. Biol. 3, 695-701, (1991)
[Non-Patent Document 6] Nakashima et al., Biochem. Pharm. 33, 3345-3352, (1984)
[Non-Patent Document 7] Friedman, Amidon., Pharm. Res., 6, 1043-1047, (1989)
[Non-Patent Document 8] Okano et al., J. Biol. Chem., 261, 14130-14134, (1986)
[Non-Patent Document 9] Muranushi et al., Pharm. Res., 6, 308-312, (1989)
[Non-Patent Document 10] Friedman, Amidon., J. Control. Rel., 13, 141-146, (1990)
[Non-Patent Document 11] Terada, Inui, Tanpakusitsu Kakusan Kouso (Proteins, Nucleic acids, Enzymes), Vol. 46, No. 5, (2001)
[Non-Patent Document 12] Saito, H. et al., J. Pharmacol. Exp. Ther., 275, 1631-1637, (1995)
[Non-Patent Document 13] Saito, H. et al., Biochim. Biophys. Acta., 1280, 173-177, (1996)
[Non-Patent Document 14] Terada, T. et al., J. Pharmacol. Exp. Ther., 281, 1415-1421 (1997)
[Non-Patent Document 15] Ogihara, H. et al., Biochem. Biophys. Res. Commun. 220, 848-852, (1996)
[Non-Patent Document 16] Takahashi, K. et al., J. Pharmacol. Exp. Ther., 286, 1037-1042 (1998)
[Non-Patent Document 17] Hong, S. et al., Am. J. Physiol. Renal. Physiol., 276, F658-F665 (1999)
[Non-Patent Document 18] Cancer Res., 58, 519-525, (1998)
[Non-Patent Document 19] Millennium World Congress of Pharmaceutical Sciences, (2000)

DISCLOSURE OF THE INVENTION

The present invention was made in view of such circumstances. Specifically, an objective of the present invention is to provide antibodies that inhibit the transport activity of peptide transporters, and cell growth inhibitors comprising the antibodies as an active ingredient, particularly, cell growth inhibitors for cancers such as pancreatic cancer.

The present inventors discovered that substances which inhibit the transport activity of peptide transporters suppress cell growth. Furthermore, the present inventors discovered antibodies that inhibit the transport activity of peptide transporters. These findings show that cell growth can be suppressed by inhibiting the activity of peptide transporters using the antibodies. Suppression of peptide transporter activity is considered as an important indicator in the development of growth inhibitors against cancer cells and such.

More specifically, the present invention provides:
(1) an antibody that has ability to inhibit the transport activity of a peptide transporter;
(2) the antibody of (1), wherein the peptide transporter is PepT1 or PepT2;

(3) the antibody of (2), wherein the peptide transporter is PepT1;

(4) the antibody of any one of (1) to (3), wherein the antibody is a monoclonal antibody;

(5) a cell growth inhibitor that comprises the antibody of any one of (1) to (4) as an active ingredient;

(6) an anti-cancer agent that comprises the antibody of any one of (1) to (4) as an active ingredient;

(7) the anti-cancer agent of (6), wherein the cancer is pancreatic cancer;

(8) a method for inhibiting the transport activity of a peptide transporter, wherein the method comprises the step of contacting a cell which expresses the peptide transporter with an antibody that binds to the peptide transporter;

(9) the method of (8), wherein the peptide transporter is PepT1 or PepT2;

(10) the method of (9), wherein the peptide transporter is PepT1;

(11) a method for suppressing cell growth, wherein the method comprises the step of inhibiting the transport activity of a peptide transporter by contacting a cell that expresses the peptide transporter with an antibody that binds to the peptide transporter;

(12) the method of (11), wherein the peptide transporter is PepT1 or PepT2;

(13) the method of (12), wherein the peptide transporter is PepT1;

(14) the method of any one of (11) to (13), wherein the cell is a cancer cell; and,

(15) the method of (14), wherein the cancer cell is a pancreatic cancer cell.

The present invention provides antibodies having the ability to inhibit the transport activity of peptide transporters. Peptide transporters of the present invention are not particularly limited; however, they are preferably peptide transporters which incorporate peptides into cells using proton motive force. More preferably, they are PepT1 or PepT2, and most preferably, they are PepT1.

The nucleotide and amino acid sequences of PepT1 and PepT2 are already known (human PepT1: GenBank XM_007063 (J. Biol. Chem., 270(12):6456-6463, (1995)); and human PepT2: GenBank XM_002922 (Biochim. Biophys. Acta., 1235:461-466, (1995))).

The antibodies of the present invention having the ability to inhibit the transport activity of peptide transporters are not particularly limited, as long as they can inhibit peptide transporter-mediated transport (for example, peptide transporter-mediated peptide uptake into cells). Peptide transporter-mediated transport inhibition does not require complete blockage of peptide transport. A decrease in the amount of peptide transported would be sufficient.

There are no limitations on the antibodies of the present invention, as long as they can bind to peptide transporters and inhibit the transport activities of the peptide transporters. Mouse antibodies, rat antibodies, rabbit antibodies, sheep antibodies, camel antibodies, chimeric antibodies, humanized antibodies, human antibodies, and such may be suitably used. The antibodies may be polyclonal or monoclonal, but monoclonal antibodies are preferred in view of the stable production of homogeneous antibodies. Polyclonal antibodies and monoclonal antibodies can be produced by methods well known to those skilled in the art.

Hybridomas that produce monoclonal antibodies can be prepared as follows using basically conventional techniques. Specifically, the hybridomas can be prepared by (1) conducting immunization using a desired antigen, or cells expressing a desired antigen, as the sensitizing antigen according to normal immunization methods; (2) fusing the obtained immunized cells with conventional parent cells by normal cell fusion methods; and (3) screening for monoclonal antibody-producing cells (hybridomas) using normal screening methods. For example, mammalian animals such as mice, rats, rabbits, sheep, and monkeys can be used as animals to be immunized. Antigens can be prepared according to conventional methods such as methods using baculoviruses (e.g., WO 98/46777). When peptide transporters expressed on a baculoviris membrane are used as an immunogen, gp64 transgenic mice may be used as the immunized animal (International Patent Application No. WO 03/104453).

Hybridomas can be produced, for example, according to the method of Milstein et al. (Kohler, G and Milstein, C., Methods Enzymol. (1981) 73: 3-46). When the antigen has low immunogenicity, immunization can be performed by linking it to a macromolecule with immunogenicity, such as albumin.

Recombinant antibodies can also be used, which can be produced by (1) cloning an antibody gene from a hybridoma; (2) incorporating the antibody gene into an appropriate vector; (3) introducing the vector into a host; and (4) producing the recombinant antibodies by genetic engineering techniques (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the variable regions (V regions) of antibodies are synthesized from hybridoma mRNAs using reverse transcriptase. When DNAs encoding a V region of an antibody of interest are obtained, they are linked to DNAs encoding an antibody constant region (C region) of interest, and then incorporated into expression vectors. Alternatively, DNAs encoding an antibody V region can be incorporated into expression vectors comprising DNAs of an antibody C region. The DNAs are incorporated into expression vectors such that expression is controlled by expression regulatory regions such as enhancers and promoters. Host cells are then transformed with these expression vectors to express the antibodies.

In the present invention, recombinant antibodies artificially modified to reduce xenoantigenicity against humans can be used. Examples of such include chimeric antibodies and humanized antibodies. These modified antibodies can be produced using known methods. A chimeric antibody is an antibody comprising the antibody heavy chain and light chain variable regions of a nonhuman mammal such as a mouse, and the antibody heavy chain and light chain constant regions of a human. A chimeric antibody can be obtained by (1) ligating the DNA encoding a variable region of a mouse antibody to the DNA encoding a constant region of a human antibody; (2) incorporating them into an expression vector; and (3) introducing the vector into a host for production of the antibody.

A humanized antibody, which is also called a reshaped human antibody, is obtained by transplanting a complementarity determining region (CDR) of an antibody of a nonhuman mammal such as a mouse, into the CDR of a human antibody. Conventional genetic recombination techniques for the preparation of such antibodies are known. Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA which encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected when the CDR forms a favorable antigen-binding site. As necessary, amino acids in the framework region of an antibody variable region may be substituted such that the CDR of a reshaped human antibody forms an appropriate antigen-binding site (Sato, K. et al., Cancer Res. (1993) 53, 851-856).

Those skilled in the art can determine the CDRs by well-known techniques, for example, using the database of antibody amino acid sequences prepared by Kabat et al. ("Sequences of Proteins of Immunological Interest" U.S. Dept. Health and Human Services, 1983) to analyze the homology.

Methods for obtaining human antibodies are also known. For example, desired human antibodies retaining antigen-binding activity can be obtained by (1) sensitizing human lymphocytes in vitro with antigens of interest or cells expressing antigens of interest; and (2) fusing the sensitized lymphocytes with human myeloma cells such as U266 (see Examined Published Japanese Patent Application No. (JP-B) Hei 1-59878). Alternatively, a desired human antibody can also be obtained by using a desired antigen to immunize a transgenic animal that comprises the entire repertoire of human antibody genes (see International Patent Application WO 93/12227, WO 92/03918, WO 94/02602, WO 94/25585, WO 96/34096, and WO 96/33735). Furthermore, techniques to obtain human antibodies by panning a human antibody library are known. For example, the variable region of a human antibody is expressed as a single chain antibody (scFv) on the surface of a phage using phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are known, appropriate expression vectors to which these sequences are inserted can be constructed to obtain human antibodies. Such methods are well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. Known animal cells include (1) mammalian cells such as CHO, COS, myeloma, baby hamster kidney (BHK), HeLa, and Vero cells; (2) amphibian cells such as *Xenopus oocytes*; or (3) insect cells such as sf9, sf21, and Tn5. Known plant cells include cells derived from the *Nicotiana* genus such as *Nicotiana tabacum*, which can be cultured as callus. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. By transferring the antibody genes of interest into these cells using transformation, and then culturing the transformed cells in vitro, the antibodies can be obtained.

Furthermore, the antibody may be an antibody fragment or a modified antibody thereof, as long as it binds to PepT and inhibits its function. For example, the antibody fragment may be Fab, F(ab')2, Fv, or single chain Fv (scFv) or a diabody, in which Fv from H or L chains are ligated by an appropriate linker. More specifically, the antibody fragment is obtained by (1) treating the antibody with enzymes such as papain and pepsin; (2) transferring it into an expression vector; and then (3) expressing it in an appropriate host cell (see, for example, Co, M. S. et al., J. Immunol. (1994) 152, 2968-2976; Better, M. & Horwitz, A. H. Methods in Enzymology (1989) 178, 476-496, Academic Press, Inc.; Plueckthun, A. & Skerra, A. Methods in Enzymology (1989) 178, 476-496, Academic Press, Inc.; Lamoyi, E., Methods in Enzymology (1989) 121, 663-669; and Bird, R. E. et al., TIBTECH (1991) 9, 132-137). scFv can be obtained by ligating the V regions of the antibody H-chain and L-chain. In scFv, the V regions of the H chain and L chain are ligated via a linker, preferably via a peptide linker (Huston, J. S. et al., Proc. Natl. Acad. Sci. U.S.A (1988) 85, 5879-5883). The V regions of the scFv H chain and L chain may be derived from any of the antibodies described herein. The peptide linker used to ligate the V regions may be, for example, any single-chain peptide consisting of 12 to 19 residues. DNA encoding scFv can be amplified by PCR using as a template either whole DNA, or a partial DNA encoding a desired DNA, selected from a DNA encoding the H chain or the V region of the H chain of the above antibody, and a DNA encoding the L chain or the V region of the L chain of the above antibody; and using a primer pair that defines the both ends. Further amplification can be subsequently conducted using the combination of DNA encoding the peptide linker portion, and the primer pair that defines both ends of the DNA to be ligated to the H chain and the L chain respectively. Once DNAs encoding scFvs are constructed, expression vectors containing the DNAs, and hosts transformed by these expression vectors, can be obtained according to conventional methods. Furthermore, scFvs can be obtained according to conventional methods using the resulting hosts. These antibody fragments can be produced in hosts by obtaining genes encoding the antibody fragments and expressing them in a manner similar to that outlined above. Diabodies are dimers formed by linking two fragments (such as scFvs; hereinafter referred to as diabody-constituting fragments), in which one variable region is linked to the other variable region via a linker or such. Ordinarily, diabodies comprise two VLs and two VHs (Holliger, P. et al., Proc. Natl. Acad. Sci. USA, 90, 6444-6448 (1993); EP 404097; WO 93/11161; Johnson et al., Method in Enzymology, 203, 88-98, (1991); Holliger et al., Protein Engineering, 9, 299-305, (1996); Perisic et al., Structure, 2, 1217-1226, (1994); John et al., Protein Engineering, 12(7), 597-604, (1999); Holliger et al., Proc. Natl. Acad. Sci. USA., 90, 6444-6448, (1993); Atwell et al., Mol. Immunol. 33, 1301-1312, (1996)).

Antibodies bound to various molecules such as polyethylene glycol (PEG) may be used as modified antibodies. Furthermore, cytotoxic substances such as radioisotopes, chemotherapeutic agents, and bacteria-derived toxins may be attached to the antibodies. Such modified antibodies can be obtained by chemically modifying the obtained antibodies. Methods for antibody modification have been established in the art.

Antibodies used in the present invention may be bispecific antibodies. Bispecific antibodies may be those that comprise antigen binding sites which recognize different epitopes of a peptide transporter molecule. Alternatively, one antigen binding site may recognize a peptide transporter, while another antigen binding site may recognize a cytotoxic substance, such as a radioactive substance, chemotherapeutic agent, or cell-derived toxin. Bispecific antibodies can be produced by joining the HL pairs from two types of antibodies, or by fusing hybridomas that produce different monoclonal antibodies to generate bispecific antibody-producing fusion cells. Furthermore, bispecific antibodies can be produced by genetic engineering techniques.

Alternatively, antibodies with modified sugar chains may also be used in the present invention. Techniques for modifying antibody sugar chains are already known (for example, WO 00/61739, WO 02/31140). The "antibodies" in the present invention include such antibodies.

Antibodies expressed and produced as described above can be purified by conventional methods for purifying normal proteins. Antibodies can be separated and purified by, for example, appropriately selecting and/or combining affinity columns such as a protein A column, or a chromatography column, filtration, ultrafiltration, salt precipitation, dialysis, and such (Antibodies A Laboratory Manual. Ed Harlow, David Lane, Cold Spring Harbor Laboratory, 1988).

Conventional means can be used to measure the antigen-binding activity of the antibodies (Antibodies A Laboratory Manual. Ed Harlow, David Lane, Cold Spring Harbor Laboratory, 1988). For example, an enzyme linked immunosorbent assay (ELISA), an enzyme immunoassay (EIA), a radioimmunoassay (RIA), or a fluoroimmunoassay may be used.

Whether a particular molecule binds to a peptide transporter can be determined using conventional methods. Examples of conventional methods include immunoprecipitation, West-Western blotting, ELISA, EIA, RIA, fluoroimmunoassay, and methods using a biosensor utilizing surface plasmon resonance effect.

Whether antibodies inhibit the transport function of peptide transporters can be determined using known methods, for example, by labeling substrates such as peptides, with a radioactive substance (e.g., $^{14}C$), fluorescent substance, or such, and then measuring the amount of substrate uptake into the peptide transporter-expressing cells (International Patent Application No. WO 03/083116, Zoku Iyakuhin no Kaihatsu 4-Yakubutsu no Seitaimakuyusou to Soshikihyoutekika I, II (Development of Pharmaceuticals 4—Transport of Pharmaceuticals Through Biological Membranes and Tissue Targetting I, II) (Terada, Hiroshi, Tsuji, Akira. et al. ed).

There are no particular limitations on the cells to be targeted by the cell growth inhibitors of the present invention, but cancer cells such as pancreatic cancer cells, liver cancer cells, lung cancer cells, esophageal cancer cells, breast cancer cells, and colon cancer cells are preferred, and pancreatic cancer cells are especially preferred. The cell growth inhibitors of the present invention are used for the purpose of treating and preventing diseases caused by cell growth, and more specifically cancers such as pancreatic cancer.

The antibodies of the present invention may be utilized not only as inhibitors of peptide transporter-mediated transport, but also as cell growth inhibitors, because they are capable of suppressing cell growth as shown in the Reference Examples. The cell growth inhibitors can be administered either orally or parenterally, but are preferably administered parenterally. Specific examples include injections, transnasal administrations, transpulmonary administrations, and transdermal administrations. For example, injections can be administered systemically or locally by intravenous injection, intramuscular injection, intraperitoneal injection, or subcutaneous injection. Furthermore, the method of administration can be selected appropriately according to the age and symptoms of the patient. A single dose can be selected, for example, from within the range of 0.0001 mg to 1,000 mg per kg body weight. Alternatively, the dose can be selected, for example, from within the range of 0.001 to 100,000 mg per patient. However, the dose of a therapeutic agent of the present invention is not limited to these examples. Furthermore, the therapeutic agents of the present invention can be formulated according to standard methods (see, for example, Remington's Pharmaceutical Science, latest edition, Mark Publishing Company, Easton, U.S.A.), and may comprise pharmaceutically acceptable carriers and additives.

BEST MODE FOR CARRYING OUT THE INVENTION

Hereinafter, the present invention is specifically illustrated with reference to Examples, but it is not to be construed as being limited thereto.

EXAMPLE 1

Production of Anti-PepT1 Antibodies Using gp64 Transgenic Mice (TgM)

Primary immunization was performed by subcutaneously injecting a PBS suspension containing PepT1-BV equivalent to a 1 mg protein and 200 ng of pertussis toxin into gp64 TgM (International Patent Application No. WO 03/104453). Subsequent immunizations were performed by subcutaneously injecting PepT1-BV equivalent to a 500 µg protein (not containing the pertussis toxin) prepared in a similar manner. The final immunization was performed by injecting PepT1-BV equivalent to a 250 µg protein via the tail vein. Spleen cells were prepared from these mice and were fused with mouse P3U1 cells by a standard polyethylene glycol method. Screening was performed using FACS with BaF/3-PepT1 cells. Furthermore, monoclonal antibodies (clones 113, 119, and 253) which specifically bind to PepT1 were established with a FACS using BaF/3-PepT2 cells.

EXAMPLE 2

Determining the Ability to Inhibit PepT1 Transport Activity $[^{14}C]$ Glycylsarcosine was diluted with HBSS (pH6.0) to a final concentration of 50 µM to prepare a substrate solution. Mouse monoclonal antibodies (clones 119, 253, and 113), which recognize the extracellular region of human PepT1, were diluted with PBS to a final concentration of 200 µg/mL to prepare antibody solutions. 20 µL of a solution of budding baculovirus expressing PepT1 (50 µg protein), the N terminus of which is attached to a His-tag, and 20 µL of each of the antibody solutions were mixed, and pre-incubated at 37° C.

for one hour. 160 μL of the substrate solution pre-warmed to 37° C. was added to the virus solution to initiate the reaction. One minute later, 1 mL of ice-cold HBSS (pH7.4) (hereinafter referred to as "quenching solution") was added to stop the reaction. The virus-containing reaction solution was immediately filtered by suction through a mixed cellulose membrane filter, and then washed twice with 5 mL of the quenching solution. The membrane filters were transferred into liquid scintillation vials, and 5 mL of Clear-sol I was added to dissolve the filters. After dissolution, the radioactivity on the filters was measured on a liquid scintillation counter. To measure non-specific adhesion to the filter, the quenching solution was added in a similar procedure before the substrate solution was added, and the measured value was subtracted from each of the values obtained from the experiments described above.

Figure 1:
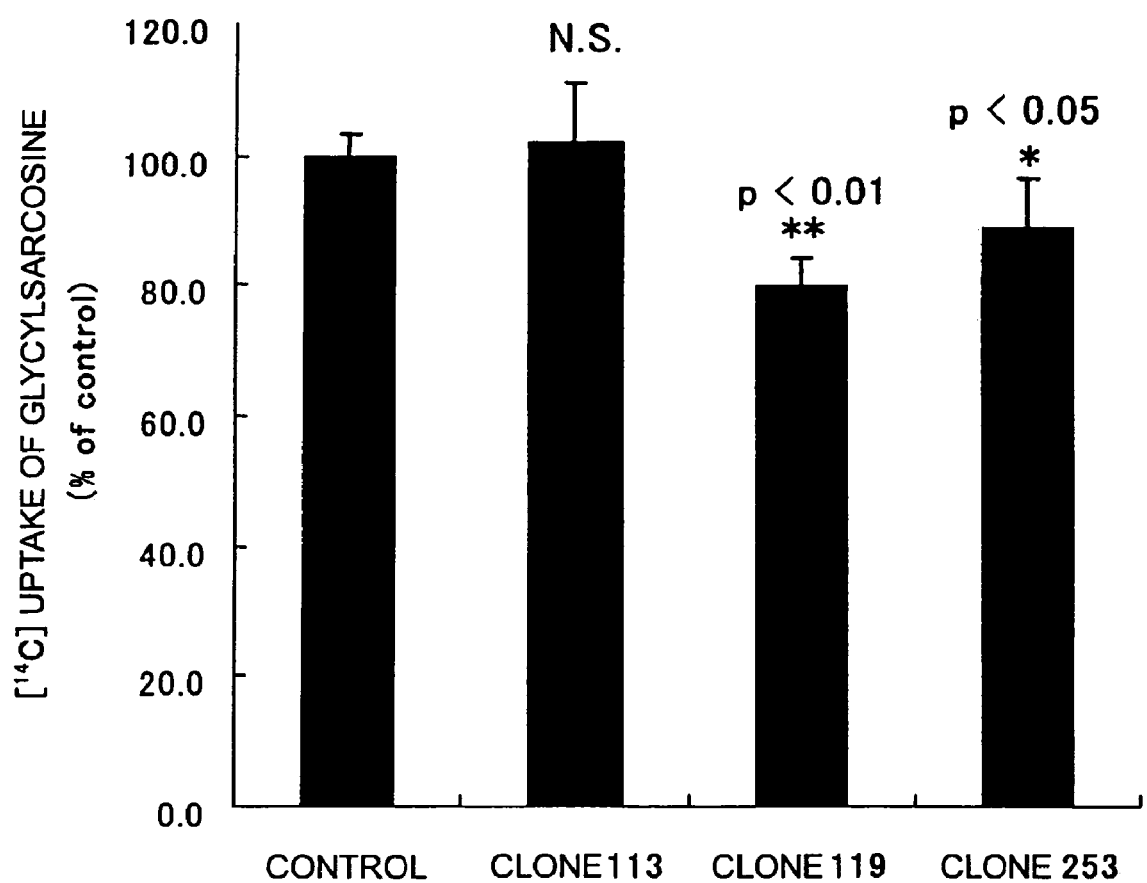
FIG. 1 is a graph showing the results of detecting the inhibition of PepT1 activity by anti-human PepT1 monoclonal antibodies in PepT1-expressing viruses. The PepT1 activity on viral membranes was measured as the amount of $[^{14}C]$ glycylsarcosine uptake by the viruses. The data are shown as an average±S.D. (n=3 to 4).

The inhibition of PepT1 activity by anti-human PepT1 monoclonal antibodies is shown in FIG. 1. As a control, the PepT1 activity in the absence of the antibodies was indicated as 100. Among the three types of anti-human PepT1 monoclonal antibodies, clone 119 inhibits approximately 20% of the PepT1 activity, and clone 253 inhibits approximately 10% of the activity in comparison to the control. The PepT1 activity inhibition was statistically significant (Student t-test). The above revealed that anti-PepT1 antibodies may have the ability to inhibit PepT1 transport activity.

SEQ ID NO: 1 represents the amino acid sequence of the heavy-chain variable region of clone 119.

REFERENCE EXAMPLE 1

AT-264's Inhibitory Effect on PepT1 Activity

AT-264 has a structure represented by the structural formula below. The following experiment confirmed that the compound is a peptide transporter (PepT) inhibitor.

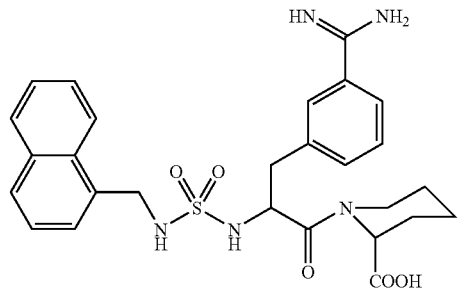

Figure 2:
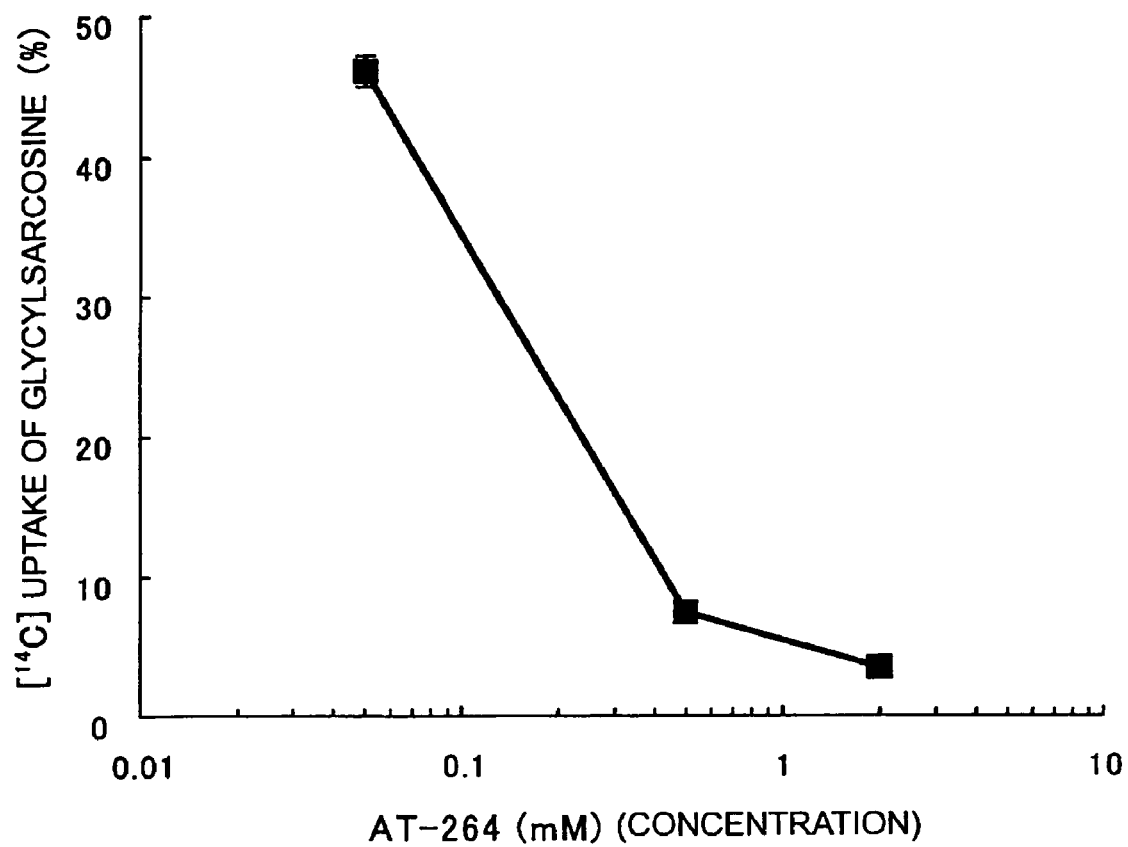
FIG. 2 is a graph showing the PepT1 inhibiting ability of AT-264 in BaF3 cells.

The ability of AT-264 to inhibit PepT1 was examined by forcedly expressing human PepT1 in mouse bone marrow-derived BaF3 cells (hereinafter abbreviated as BaF3/PepT1). The results showed that the uptake of the radioactive substrate [$^{14}$C] glycylsarcosine into cells was inhibited in a concentration-dependent manner (FIG. 2). Accordingly, AT-264 was found to inhibit PepT1 functions.

REFERENCE EXAMPLE 2

The Cell Growth Inhibitory Effect of AT-264 Against Human Pancreatic Cancer Cell Line AsPC-1

AT-264 was dissolved in RPMI1640-10 mM Hepes (hereinafter, abbreviated as 'the medium') containing 0.5% ethanol and 0.5% DMSO to prepare 2.5 mM AT-264 solution. Then, this solution was diluted with the medium to prepare 0.625 mM and 0.0625 mM AT-264 solutions.

A $5 \times 10^4$ cells/mL solution of human pancreatic cancer cell line AsPC-1 was prepared using a medium containing 50% FBS. This suspension was seeded at 40 μL/well ($2 \times 10^3$ cells) onto a 96-well plate pre-coated with Collagen type I, and 160 μL of the AT-264 solution was added. This was cultured for six days in a $CO_2$ incubator (on the second day of culture, 100 units/mL penicillin and 0.1 mg/mL streptomycin were added). On the sixth day of culture, the number of viable cells was quantified by MTS assay.

Figure 3:
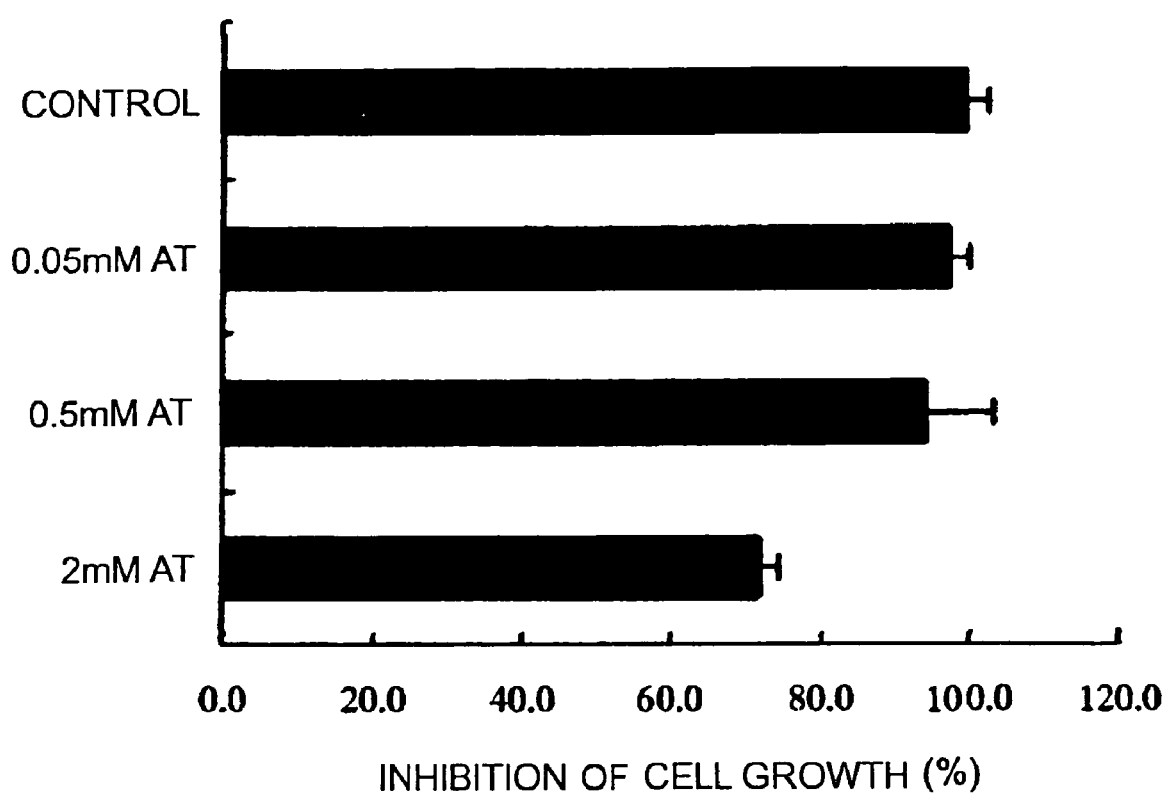
FIG. 3 is a graph showing the cell growth inhibitory effect of AT-264 against human pancreatic cancer cell line AsPC-1. The data are shown as an average±S.D. (n=3 to 4).

The results of the cell growth experiment are shown in FIG. 3. Cell growth inhibition was confirmed to be approximately 30% in the presence of 2 mM AT-264, and was present even in the presence of 0.5 mM AT-264, although slight. Morphological changes to AsPC-1 were not observed under the microscope, even in the presence of AT-264. Furthermore, the results of RT-PCR indicated that in AsPC-1, PepT1 expression was greater than PepT2. Accordingly, cell growth inhibition by AT-264 was considered to be due to the inhibition of PepT1 function, and not to non-specific cytotoxicity.

REFERENCE EXAMPLE 3

Inhibitory Effect of AT-264 on PepT2 Activity

Figure 4:
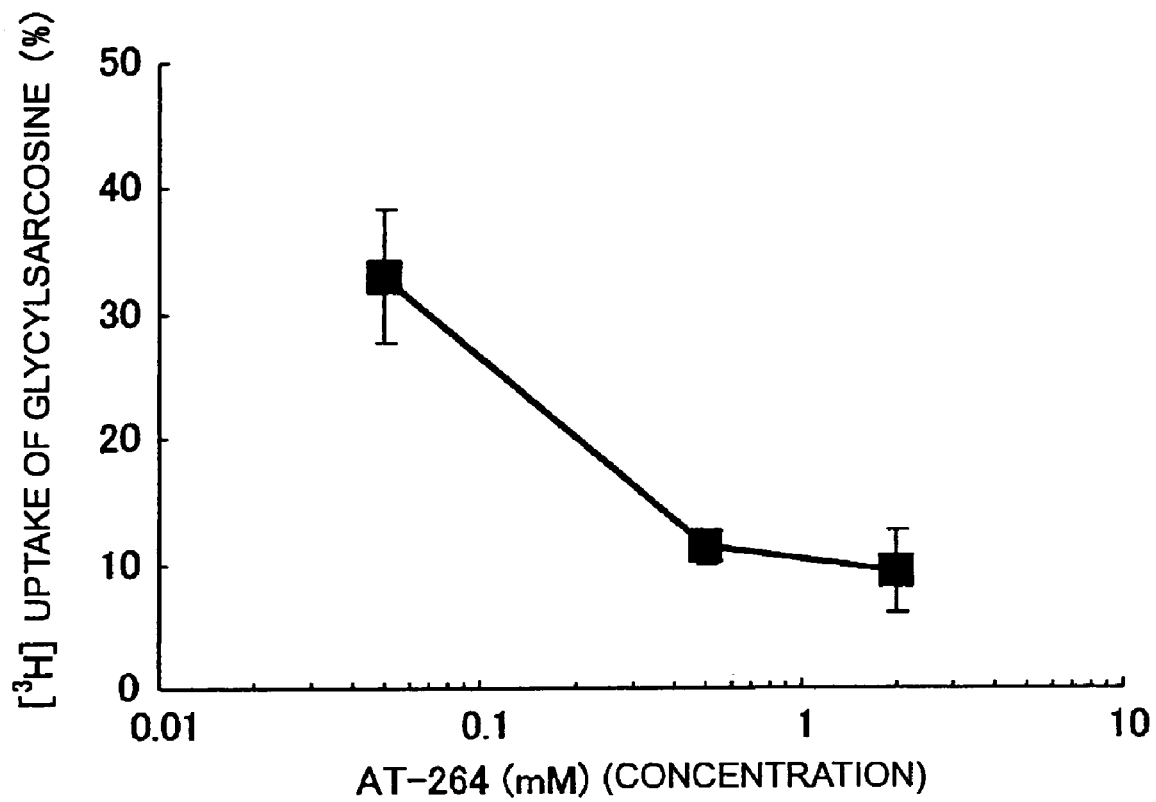
FIG. 4 is a graph showing the PepT2 inhibiting ability of AT-264 in BaF3/PepT2. The data are shown as an average±S.D. (n=3 to 4).

The ability of AT-264 to inhibit PepT2 was examined using a murine bone marrow-derived cell line BaF3 in which human PepT2 is forcedly expressed (hereinafter, abbreviated as BaF3/PepT2). As a result, the uptake of the radioactive substrate [$^3$H] glycylsarcosine into cells was inhibited in a concentration-dependent manner (FIG. 4). Accordingly, AT-264 was found to inhibit the function of not only PepT1, but also of PepT2.

REFERENCE EXAMPLE 4

Cell Growth Inhibitory Effect of AT-264 on Human Pancreatic Cancer Cell Line BxPC-3

AT-264 was dissolved in RPMI1640-10 mM Hepes with 100 units/mL penicillin and 0.1 mg/mL streptomycin (hereinafter, abbreviated as 'the medium') containing 0.5% ethanol and 0.5% DMSO to prepare 2.5 mM AT-264 solution. Furthermore, this solution was diluted with the medium to prepare 0.625 mM and 0.0625 mM AT-264 solutions.

$5 \times 10^4$ cells/mL solution of BxPC-3 was prepared using the medium containing 50% FBS. This suspension was seeded at 40 μL/well ($2 \times 10^3$ cells) onto a 96-well plate pre-coated with Collagen type I, and 160 μL of AT-264 solution was added. This was cultured for six days in a $CO_2$ incubator, and on the sixth day of culture, the number of viable cells was quantified by MTS assay.

Figure 5:
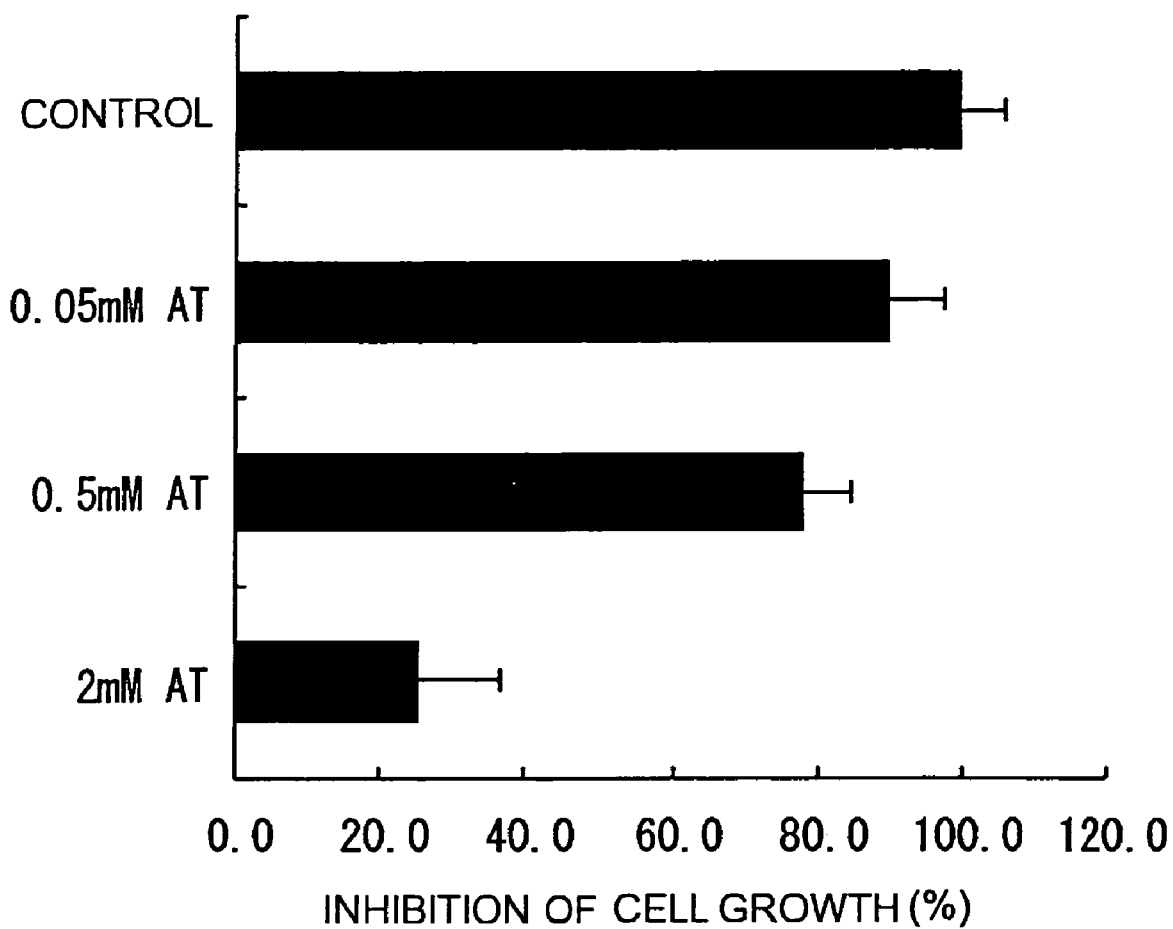
FIG. 5 is a graph showing the cell growth inhibitory effect of AT-264 against human pancreatic cancer cell line BxPC-3. The data are shown as an average±S.D. (n=6).

The results of the cell growth experiment are shown in FIG. 5. Cell growth inhibition was confirmed to be approximately 75% in the presence of 2 mM AT-264, and approximately 20% even in the presence of 0.5 mM AT-264. Morphological changes to BxPC-3 were not observed under the microscope, even in the presence of AT-264. Furthermore, the RT-PCR results showed that PepT2 expression was greater than PepT1 expression in BxPC-3. Accordingly, cell growth inhibition by AT-264 was considered to be due to the inhibition of PepT2 function, and not due to cytotoxicity. Therefore, it is clear that substances which inhibit the transport activity of PepT1 or PepT2 also serve as cell growth inhibitors.

REFERENCE EXAMPLE 5

Production of gp64 Transgenic Mice gp64 transgenic mice were produced according to the method described in International Patent Application No. WO 03/104453. Specifically, the mice were produced by the procedures described below.

1) Construction of the gp64 Transgenic Vector

Figure 6:
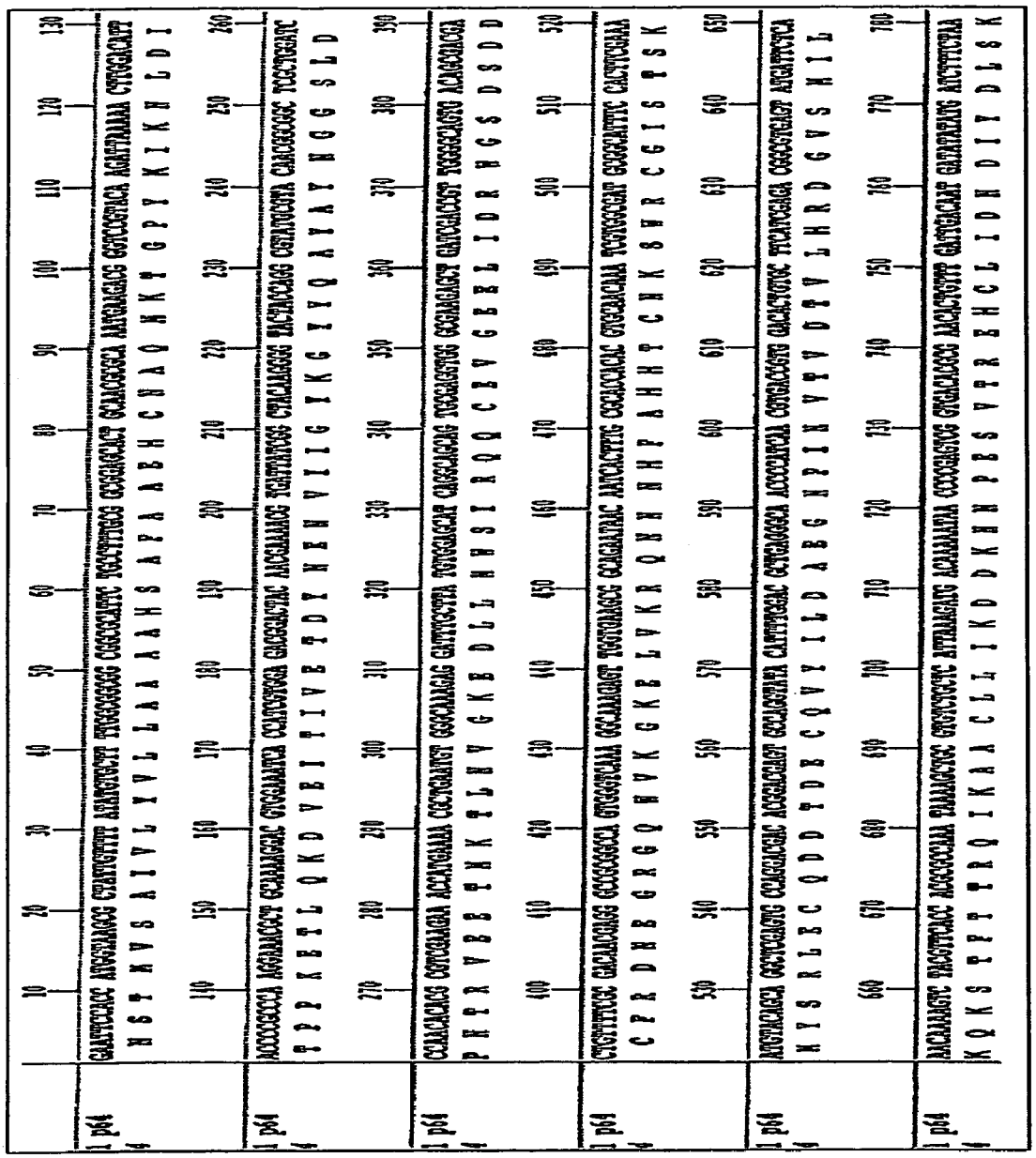
FIG. 6 shows the nucleotide sequence of the gp64 gene construct.
Figure 7:
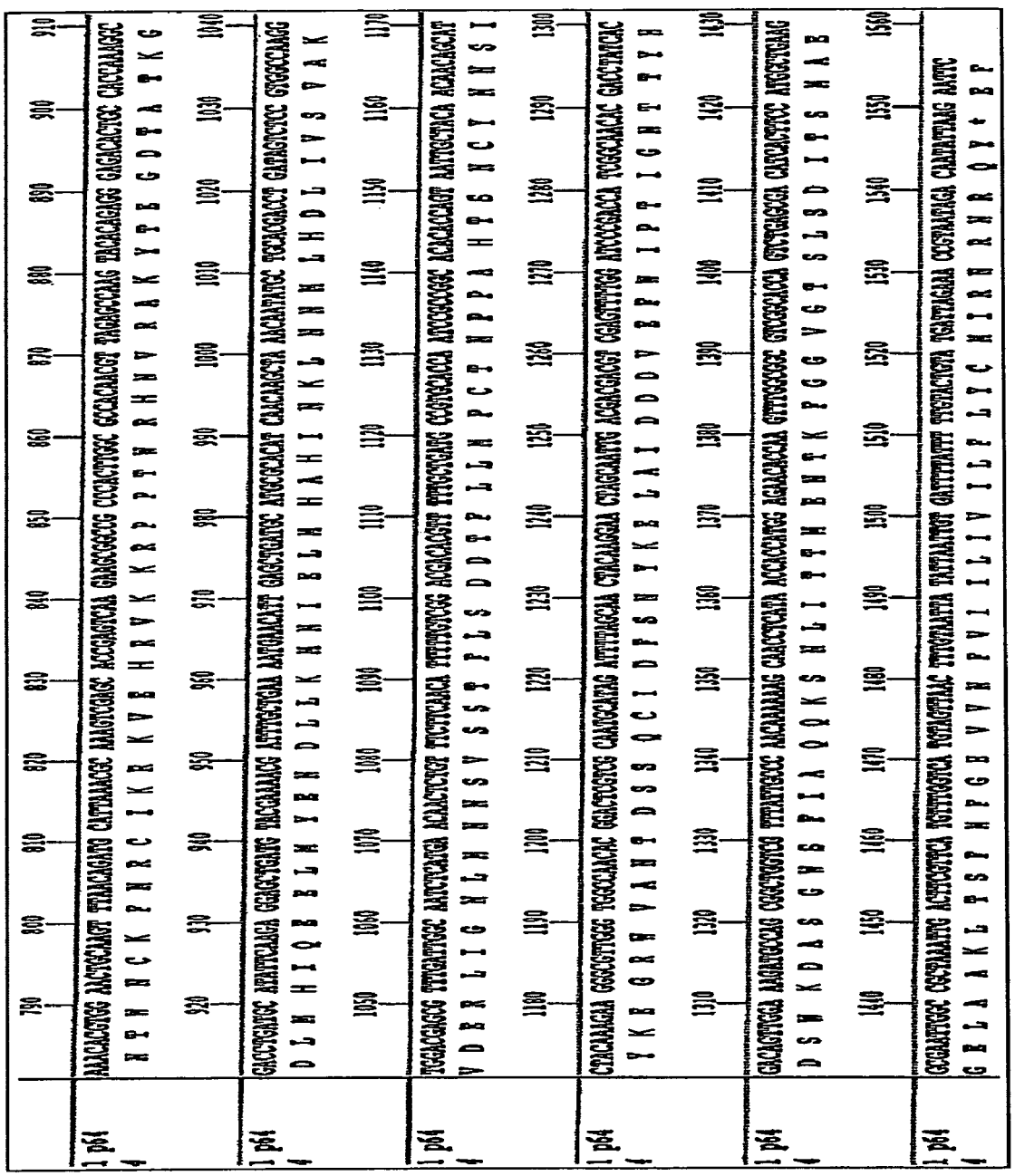
FIG. 7 is a continuation of FIG. 6.

PCR was performed using the gp64 gene sequence (GenBank Acc. No. 9627742) as a template, under the conditions described below. As a 5' primer, 64F1 which comprises an EcoRI recognition sequence and a KOZAK sequence at the 5' end was used (FIG. 6); and as a 3' primer, 64R1 which comprises an EcoRI recognition sequence at the 5' end was used (FIG. 7).

The PCR reaction solution had the following composition: 5 µL of 10×ExTaq buffer; 4 µL of dNTP that comes with ExTaq; 1 µL of 64F1 (10 µmol/L); 1 µL of 64R1 (10 µmol/L); 1 µL of pBac-N-blue (500 µg/µL); 0.5 µL of ExTaq (5 unit/µL); and 37.5 µL of diw. The reaction sequence was as follows:
94° C. 5 min→
(94° C. 15 sec, 57° C. 30 sec, and 72° C. 30 sec)×25 cycles→
72° C. 7 min→
4° C. (forever)

The amplified band was subcloned into pGEM-T easy, and was used to transform $E.\ coli$ DH5α. Colony PCR was performed using the T7 and SP6 primers. Then, nucleotide sequences of the clones that have been confirmed to comprise inserts were analyzed on the ABI Prism 377 DNA sequencer, using the BigDye Cycle Sequence Kit and T7 primer or SP6 primer to identify a clone comprising the gene of interest. After the clone was confirmed not to contain any mutations in its nucleotide sequence, a gp64-comprising fragment was excised from this clone using EcoRI. For transformation of $E.\ coli$ DH5α, this fragment was inserted into pCAGGS1 which also had been cleaved with EcoRI. The produced clone, which was as designed, was cultured overnight in 250 mL of LB medium at 37° C., and purified using the Endofree MAXI Kit to yield 581.6 µg of plasmid.

2) Gene Introduction

Figure 8:
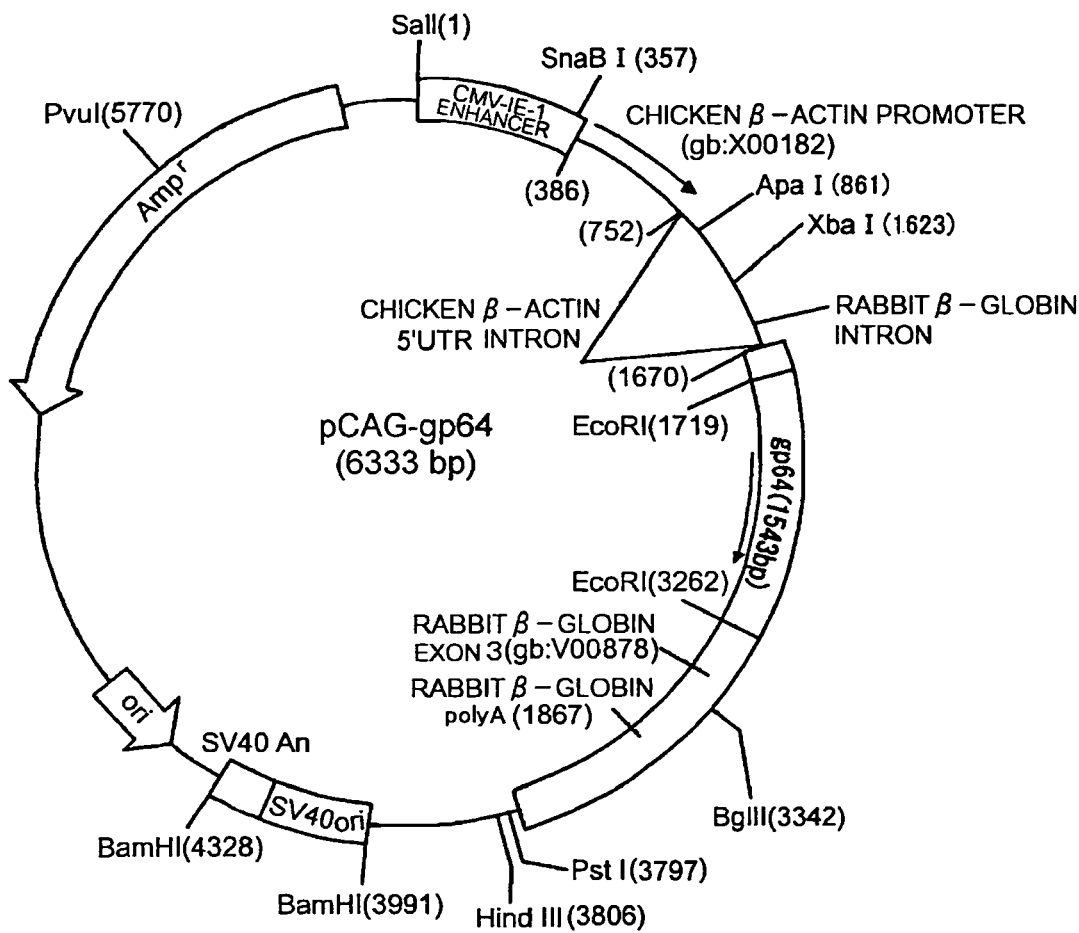
FIG. 8 shows the structure of the pCAG-gp64 vector construct.

The DNA fragment to be injected was prepared as described below. First, the gp64 gene-harboring pCAGGS vector (pCAG-gp64; FIG. 8) was treated with SalI and PstI to excise a gp64 gene-comprising fragment (approximately 3.8 kb). This fragment (approximately 3.8 kb) was recovered using the Gel Extraction Kit (QIAGEN), and then diluted to 3 ng/µL with PBS to prepare the DNA fragment to be injected.

Mouse pronuclear stage eggs, to which the DNA fragment was injected, were collected as described below. Superovulation treatment was carried out by intraperitoneally administering 5 i.u. of PMSG to female Balb/c mice (Clea Japan) initially, and then intraperitoneally administering 5 i.u. of hCG 48 hours later. These female mice were mated with male mice of the same strain. Mating was confirmed by the presence of a plug the following morning, and the oviducts of mice were perfused to collect the mouse pronuclear stage eggs.

The DNA fragment to be injected was injected into pronuclear stage eggs using a micromanipulator (Modern Techniques in Gene Targeting (Yodosha), 190-207, 2000). The day after the DNA fragment was injected into 373 BALB/c embryos, 216 embryos that had developed to the two-cell stage were transplanted into day 1 pseudopregnant recipient females, approximately ten embryos per oviduct (20 embryos per individual).

REFERENCE EXAMPLE 6

Preparation of PepT1—Expressing Budding Baculovirus (PepT1-BV)

The PepT1-expressing budding baculovirus to be used as the immunogen was prepared as described below. PepT1 is a transporter which functions as a membrane protein. The structure of PepT1 is well known (GenBank XM_007063; J. Biol. Chem. 270(12): 6456-6463 (1995)).

A full-length PepT1 gene was isolated from a human renal library using PCR. The transfer vector, pBlueBacHis-PepT1, was prepared by inserting the full-length human PepT1 gene into pBlueBacHis2A (Invitrogen). Using the Bac-N-Blue Transfection Kit (Invitrogen), the transfer vector was then introduced into Sf9 cells, along with a Bac-N-Blue DNA, to produce recombinant viruses for human PepT1 expression. Specifically, 4 µg of pBlueBacHis-PepT1 was added to the Bac-N-Blue DNA, and then 1 mL of Grace's medium (GIBCO) and 20 µL of the Cell FECTIN reagent were added, followed by mixing. The mixture was left to stand at room temperature for 15 minutes, and then added dropwise to $2 \times 10^6$ Sf9 cells, which had been pre-washed once with Grace's medium. After letting the cells stand at room temperature for four hours, an additional 2 mL of complete medium (Grace's medium containing 10% fetal bovine serum (Sigma), 100 units/mL of penicillin, and 100 µg/mL streptomycin (GIBCO-BRL)) was added, and the cells were then incubated at 27° C. Recombinant viruses for human PepT1 expression were then produced by homologous recombination, and purified twice according to the instructions attached to the kit, to obtain a virus stock of the recombinant virus.

Budding viruses which express human PepT1 were prepared as described below. The recombinant virus thus prepared was used to infect 500 mL of Sf9 cells ($2 \times 10^6$/mL) at MOI=5. After culturing at 27° C. for three days, the cultured medium was centrifuged at 800×g for 15 minutes, and the cells and cell debris were removed. The supernatant collected by centrifugation was further centrifuged at 45,000×g for 30 minutes. The obtained precipitate were suspended in PBS, and then centrifuged at 800×g for 15 minutes to remove the cell components. The budding virus fraction was obtained by centrifuging the supernatant at 45,000×g for another 30 minutes, and then resuspending the precipitate in PBS.

INDUSTRIAL APPLICABILITY

The present inventors discovered that antibodies which bind to PepT have the ability to inhibit the transport activity of peptide transporters. These antibodies may be utilized as cell growth inhibitors, for example, for treating or preventing cancer.

The invention claimed is:

1. A method for inhibiting peptide transporter activity, the method comprising contacting
   (a) an isolated antibody or antigen-binding fragment thereof that (i) binds to a PepT1 or PepT2 peptide transporter and (ii) inhibits peptide uptake into a cell expressing the peptide transporter, with
   (b) a cell expressing the peptide transporter,
wherein the antibody is a monoclonal or genetically engineered recombinant antibody, and wherein the cell is in vivo.

2. The method of claim 1, wherein the antibody is monoclonal.

3. The method of claim 1, wherein the antibody is human or humanized.

4. A method for suppressing cell growth, the method comprising contacting (a) an isolated antibody or antigen-binding fragment thereof that (i) binds to a PepT1 or PepT2 peptide transporter and (ii) inhibits peptide uptake into a cell expressing the peptide transporter, with
   (b) a cell expressing the peptide transporter, wherein the antibody is a monoclonal or genetically engineered recombinant antibody, the cell is in vivo, and growth of the cell is suppressed.

5. The method of claim 4, wherein the antibody is monoclonal.

6. The method of claim 4, wherein the antibody is human or humanized.

7. The method of claim 4, wherein the cell is a cancer cell.

8. The method of claim 4, wherein the cell is a pancreatic cancer cell.

9. The method of claim 1, wherein the cell is in a patient and the antibody of fragment thereof is administered to the patient.

10. The method of claim 4, wherein the cell is in a patient and the antibody of fragment thereof is administered to the patient.

* * * * *